(12) United States Patent
Lee (10) Patent No.: US 12,350,022 B2
(45) Date of Patent: Jul. 8, 2025

(54) SENSOR MODULE FOR MEASURING BLOOD PRESSURE, AND WRIST-WEARABLE PORTABLE BLOOD PRESSURE MEASUREMENT DEVICE USING SAME

(71) Applicant: CHARMCARE CO., LTD., Seoul (KR)

(72) Inventor: Dong Hwa Lee, Yongin-si (KR)

(73) Assignee: CHARMCARE CO., LTD., Seoul (KR)

( * ) Notice: Subject to any disclaimer, the term of this patent is extended or adjusted under 35 U.S.C. 154(b) by 868 days.

(21) Appl. No.: 17/605,882

(22) PCT Filed: Apr. 22, 2020

(86) PCT No.: PCT/KR2020/005308
§ 371 (c)(1),
(2) Date: Oct. 22, 2021

(87) PCT Pub. No.: WO2020/218819
PCT Pub. Date: Oct. 29, 2020

(65) Prior Publication Data
US 2022/0218207 A1     Jul. 14, 2022

(30) Foreign Application Priority Data
Apr. 25, 2019    (KR) ........................ 10-2019-0048750

(51) Int. Cl.
*A61B 5/021*     (2006.01)
*A61B 5/00*     (2006.01)

(52) U.S. Cl.
CPC ............ *A61B 5/021* (2013.01); *A61B 5/0004* (2013.01); *A61B 5/6824* (2013.01);
(Continued)

(58) Field of Classification Search
CPC ..... A61B 5/021; A61B 5/0004; A61B 5/6824; A61B 5/6831; A61B 5/742;
(Continued)

(56) References Cited

U.S. PATENT DOCUMENTS 6,491,647 B1 * 12/2002 Bridger ................. G01L 1/2231
128/900
10,849,555 B1 * 12/2020 Sullivan ............... A61B 5/6824
(Continued)

FOREIGN PATENT DOCUMENTS

CN    102143705 A    8/2011
CN    102596018 A    7/2012
(Continued)

OTHER PUBLICATIONS

International Search Report—PCT/KR2020/005308 dated Jul. 31, 2020.

*Primary Examiner* — Jason M Sims
*Assistant Examiner* — Kyle W. Kretzer
(74) *Attorney, Agent, or Firm* — CANTOR COLBURN LLP (57) ABSTRACT

A sensor module for blood pressure measurement includes: a substrate unit; and a first pressure sensor unit and a second pressure sensor unit coupled to the substrate unit, protruding by different distances from a reference plane of the substrate unit, and disposed adjacent to each other. Sensor module includes a control unit that controls operations of the first pressure sensor unit and the second pressure sensor unit, and measures a blood pressure in a blood pressure measurement target blood vessel based on a first pressure sensed by the first pressure sensor unit and a second pressure sensed by the second pressure sensor unit. There is a step between a reference plane of the first pressure sensor unit and a reference plane of the second pressure sensor unit. The control unit estimates a second distance indicating a distance
(Continued)

from the reference plane the first pressure sensor unit to a blood pressure measurement target blood vessel based on the first pressure, the second pressure, and the first distance, and calculates a blood pressure value in the target blood vessel based on a value obtained by multiplying the first pressure by the second distance, or a value obtained by multiplying the second pressure by a sum of the first distance and the second distance.

10 Claims, 12 Drawing Sheets

(52) U.S. Cl.
CPC ............ *A61B 5/6831* (2013.01); *A61B 5/742* (2013.01); *A61B 2562/0247* (2013.01); *A61B 2562/0261* (2013.01); *A61B 2562/043* (2013.01)

(58) Field of Classification Search
CPC .... A61B 2562/0247; A61B 2562/0261; A61B 2562/043; A61B 5/7235; A61B 5/7275; A61B 5/022
See application file for complete search history.

(56) References Cited

U.S. PATENT DOCUMENTS

| | | |
|---|---|---|
| 2003/0212335 A1 | 11/2003 | Huang |
| 2013/0144176 A1 | 6/2013 | Lee |
| 2017/0360306 A1* | 12/2017 | Narasimhan ......... A61B 5/0053 |
| 2023/0108062 A1* | 4/2023 | Lee .................... A61B 5/02141 600/485 |

FOREIGN PATENT DOCUMENTS

| | | |
|---|---|---|
| CN | 103099611 A | 5/2013 |
| CN | 103565420 A | 2/2014 |
| CN | 105232013 A | 1/2016 |
| JP | 2011239972 | 12/2011 |
| KR | 20080017176 | 2/2008 |
| KR | 101213157 | 12/2012 |
| KR | 20170008197 | 1/2017 |
| KR | 20170040034 | 4/2017 |
| KR | 101784484 | 10/2017 |
| KR | 20190022285 A | 3/2019 |

* cited by examiner

SENSOR MODULE FOR MEASURING BLOOD PRESSURE, AND WRIST-WEARABLE PORTABLE BLOOD PRESSURE MEASUREMENT DEVICE USING SAME

TECHNICAL FIELD

The present invention relates to a blood pressure measuring device, and more particularly, to a sensor module for blood pressure measurement and a wrist-worn portable blood pressure measuring device using the same.

BACKGROUND

Recently, an interest in health care is increasing, and as the number of patients with high blood pressure and low blood pressure increases, research on a wearable device for blood pressure measurement that may easily check their own blood pressure is being actively conducted.

In particular, in order to improve portability of a blood pressure measurement device, a wearable blood pressure measuring device using an optical sensor and a pressure sensor to measure blood pressure is being developed.

A conventional wearable blood pressure measuring device using the pressure sensor includes an air pump for checking a blood pressure in a wrist band worn on the wrist, and measures the blood pressure by pressing the wrist using the air pump of the wrist band. Therefore, there is a problem that causes inconvenience to a user in a pressing process for measuring the blood pressure.

SUMMARY OF INVENTION

Technical Problem

The present invention is provided to solve the problem of the related art described above, and an object of the present invention is to provide a sensor module that measures a relative pressure of the artery at a position where each pressure sensor is located, using a plurality of pressure sensors located at different heights from each other, calculates a distance from the pressure sensor to the artery using a difference in measured pressures, and then more accurately calculates a blood pressure using the calculation.

In addition, another object of the present invention is to provide a wrist-worn portable blood pressure measuring device using such a sensor module for blood pressure measurement.

However, the technical problem to be solved by the present embodiment is not limited to the technical problem described above, and other technical problems may exist.

Solution to Problem

As technical means for solving the technical problems described above, according to a first aspect of the present invention, there is provided a sensor module for blood pressure measurement, including: a substrate unit; and a first pressure sensor unit and a second pressure sensor unit coupled to the substrate unit, protruding by different distances from a reference plane of the substrate unit, and disposed adjacent to each other.

The sensor module according to the first aspect of the present invention may further include: a control unit that controls operations of the first pressure sensor unit and the second pressure sensor unit, and measures a blood pressure in a blood pressure measurement target blood vessel based on a first pressure sensed by the first pressure sensor unit and a second pressure sensed by the second pressure sensor unit. In this case, there may be a step between a reference plane of the first pressure sensor unit and a reference plane of the second pressure sensor unit. The control unit may estimate a second distance indicating a distance from the reference plane the first pressure sensor unit to the blood pressure measurement target blood vessel based on the first pressure, the second pressure, and the first distance, and calculate a blood pressure value in the target blood vessel based on a value obtained by multiplying the first pressure by the second distance, or a value obtained by multiplying the second pressure by a sum of the first distance and the second distance.

On the other hand, according to a second aspect of the present invention, there is provided a wrist-worn portable blood pressure measuring device including: a body unit in which a display unit displaying blood pressure information, a power supply unit, and a control unit are built; a wrist strap coupled to the body unit; and a sensor module for blood pressure measurement coupled to the body unit or the wrist strap. In this case, the sensor module includes a first pressure sensor unit and a second pressure sensor unit coupled to a substrate unit, protruding by a distance different from each other from a reference plane of the substrate unit, and disposed adjacent to each other.

The control unit of the wrist-worn portable blood pressure measuring device according to the second aspect of the present invention may estimate a second distance indicating a distance from the upper portion of the support unit to the blood pressure measurement target blood vessel based on the first pressure, the second pressure, and the first distance, calculate a blood pressure value in the target blood vessel based on a value obtained by multiplying the first pressure by the second distance, or a value obtained by multiplying the second pressure by a sum of the first distance and the second distance, and output the calculated blood pressure via the display.

Advantageous Effects

According to the above-described means for solving the problems of the present application, the blood pressure measuring device using the pressure sensor according to an embodiment of the present invention may measure the blood pressure only with the pressure sensor without a procedure of applying a pressure to a target point using an air pump in the blood pressure measurement process. Therefore, the user may comfortably measure blood pressure at any time.

In addition, since the blood pressure measuring device using the pressure sensor according to an embodiment of the present invention does not use the air pump that applies the pressure to measure the blood pressure, the manufacturing process is simplified, the cost is reduced, and the blood pressure measuring device may be manufactured in a compact size. Therefore, the user portability and convenience may be increased.

In addition, the sensor module for blood pressure measurement according to an embodiment of the present invention may be attached to a target point in forms of various types of wearable devices such as clothes in addition to the wrist-worn form, to be used to measure blood pressure.

BEST MODE

Hereinafter, embodiments of the present application will be described in detail with reference to the accompanying drawings so that those of ordinary skill in the art may easily implement them. However, the present application may be embodied in several different forms and is not limited to the embodiments described herein. In addition, in order to clearly explain the present application in the drawings, parts irrelevant to the description are omitted, and similar reference numerals are attached to similar parts throughout the specification.

Throughout the specification of the present application, when a part is "connected" with another part, it includes not only a case of being "directly connected" but also a case of being "electrically connected" with another element interposed therebetween.

Throughout the specification of the present application, when a member is said to be located "on" another member, this includes not only a case where a member is in contact with another member but also a case where further another member is present between the two members.

Hereinafter, an embodiment of the present invention will be described in detail with reference to the accompanying drawings.

Figure 1:
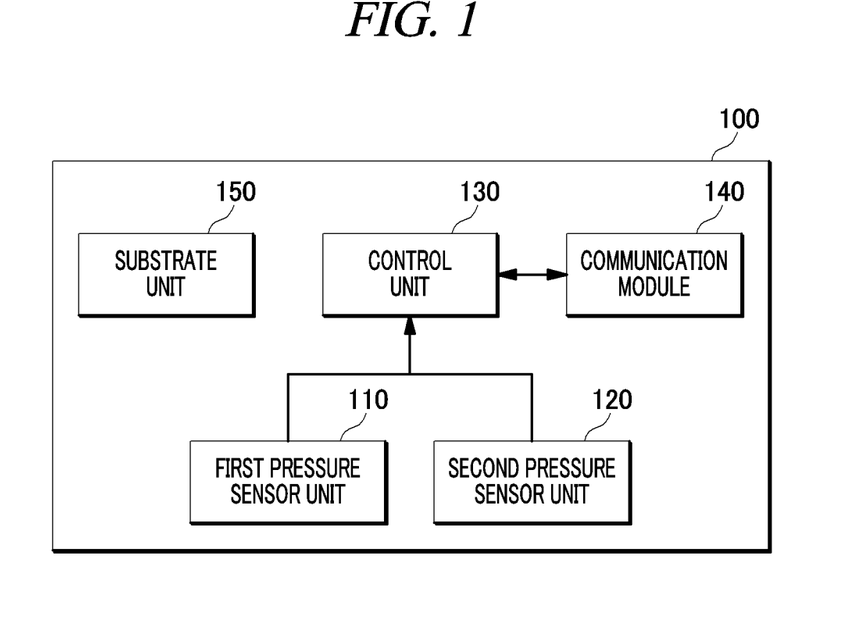
FIG. 1 is a block diagram illustrating a configuration of a sensor module for blood pressure measurement according to an embodiment of the present invention.

FIG. 1 is a block diagram illustrating a configuration of a sensor module for blood pressure measurement according to an embodiment of the present invention and FIG. 2 is a view for explaining a principle of the sensor module for blood pressure measurement according to an embodiment of the present invention.

As illustrated in the drawing, the sensor module 100 for blood pressure measurement may include a first pressure sensor unit 110, a second pressure sensor unit 120, a control unit 130, a communication module 140, and a substrate unit 150.

The first pressure sensor unit 110 and the second pressure sensor unit 120 included in the sensor module 100 protrude by different distances from a reference plane of the substrate unit 150 and are disposed adjacent to each other.

At this time, the first pressure sensor unit 110 and the second pressure sensor unit 120 each may be a strain gauge-based semiconductor thin film sensor, a capacitive thin film sensor for detecting a capacity change according to a pressure, a piezoresistive sensor using a piezo resistance effect, or other various pressure sensors.

Here, the strain gauge-based thin film sensor has an advantage that only a resistance change needs to be controlled by arranging four resistors on a diaphragm in a form of a Wheatstone bridge. The capacitive thin film sensor has an advantage of strong heat resistance and corrosion resistance, and of being able to measure a pressure with high precision when measuring the pressure. The piezoresistive sensor has advantages of high sensitivity, linearity, and reproducibility when measuring the pressure, and of being easy to mass-produce.

The control unit 130 may calculate a distance between the first pressure sensor unit 110 and the artery A, and a blood pressure of the artery A based on pressures measured by the first pressure sensor unit 110 and the second pressure sensor unit 120, and a distance difference between the first pressure sensor unit 110 and the second pressure sensor unit 120.

The communication module 140 may communicate with a communication module 240 of a body unit 200 and various external devices (servers or terminals) in communication formats set respectively to transmit and receive data.

The first pressure sensor unit 110 and the second pressure sensor unit 120 are located in the substrate unit 150. In this case, the first pressure sensor unit 110 and the second pressure sensor unit 120 protrude by different distances from the reference plane of the substrate unit 150, and are disposed adjacent to each other. Meanwhile, the control unit 130 and the communication module 140 may be coupled to the substrate unit 150 or a back surface of the substrate unit 150, or may be disposed to be included in a separate housing to which the substrate unit 150 is coupled.

The support unit 160 is located between the first pressure sensor unit 110 and the substrate unit 150 to provide a step between the first pressure sensor unit 110 and the second pressure sensor unit 120. As illustrated in FIG. 2, the step between the first pressure sensor unit 110 and the second pressure sensor unit 120 may be maintained by a height of the support unit 160. At this time, the support unit 160 may be integral with the first pressure sensor unit 110 or may be a separate configuration element. Positions of the first pressure sensor unit 110, the support unit 160, and the second pressure sensor unit 120 in the sensor module 100 of FIGS. 2 and 3 may be referred.

The sensor module 100 may be used in combination with a smart watch, a portable blood pressure measuring device, and the like. In addition, the user may measure the blood pressure with the sensor module which only comes into close contact with the body by being attached to the wrist or being inserted to clothes or the like by using fixing means such as a tape.

Figure 2A:
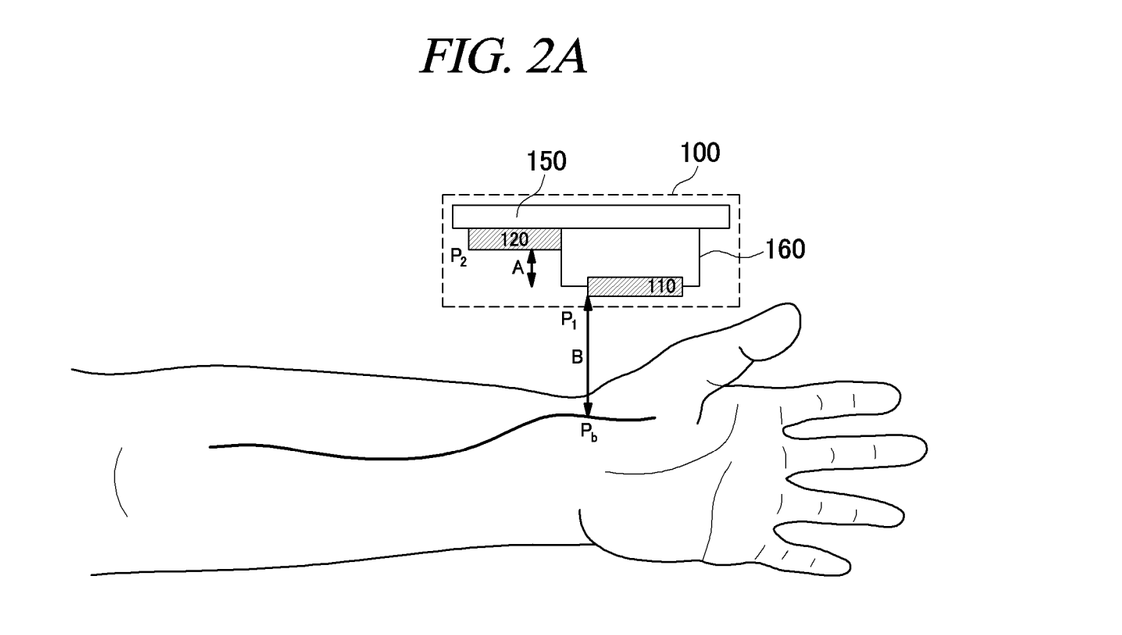
FIGS. 2a to 2e are views for explaining a principle of a sensor module for measuring the blood pressure according to an embodiment of the present invention.
Figure 2B:
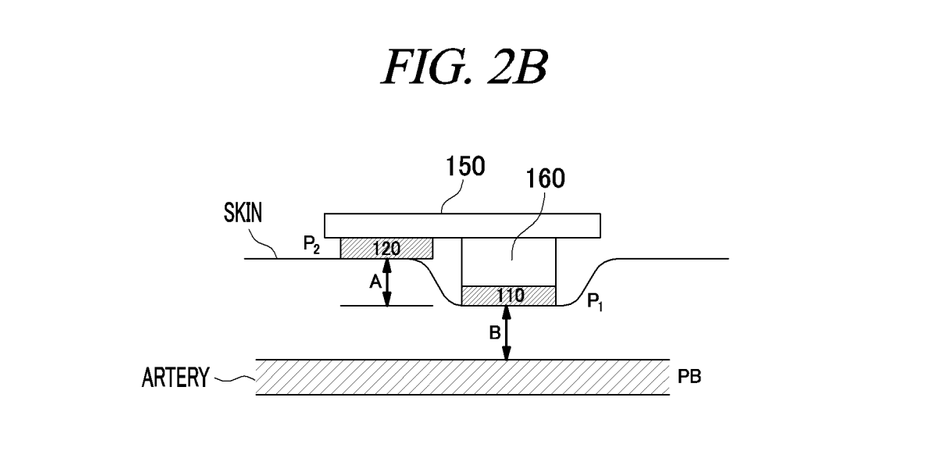

Referring to FIGS. 2a and 2b, a blood pressure of the artery A for which an actual blood pressure is to be measured is $P_b$, a pressure measured by the first pressure sensor unit 110 is $P_1$, and a pressure measured by the second pressure sensor unit 120 is $P_2$, a distance from the first pressure sensor unit 110 to the second pressure sensor unit 120 is A, and a distance from the first pressure sensor unit 110 to the artery A is B. In this case, the distance A is a predetermined constant value, $P_1$ and $P_2$ are pressures measured by the sensor module 100, and the distance B and blood pressure $P_b$ are values calculated by calculation. In the case of the distance B, since it is a distance from the first pressure sensor unit 110 to the blood vessel inside the wrist, it is a value measured differently depending on the person.

The pressure measured by the sensor module 100 is inversely proportional to the distance between the blood vessel and the sensor units 110 and 120. Therefore, the distance B from the first pressure sensor unit 110 to the artery A may be obtained by using Equation 1 below.

$$P_1 \propto \frac{P_B}{B} \quad P_2 \propto \frac{P_B}{A+B} \quad \frac{P_1}{P_2} = A + \frac{B}{B} = 1 + \frac{A}{B} \quad B = \frac{P_2}{P_1 - P_2} A \quad \text{[Equation 1]}$$

When the distance B from the first pressure sensor unit 110 to the artery A is obtained, the blood pressure $P_B$ may also be obtained by using Equation 2 below.

$$P_B \propto B*P_1 \text{ or } P_0 \propto (A+B)*P_2 \quad \text{[Equation 2]}$$

Figure 2C:
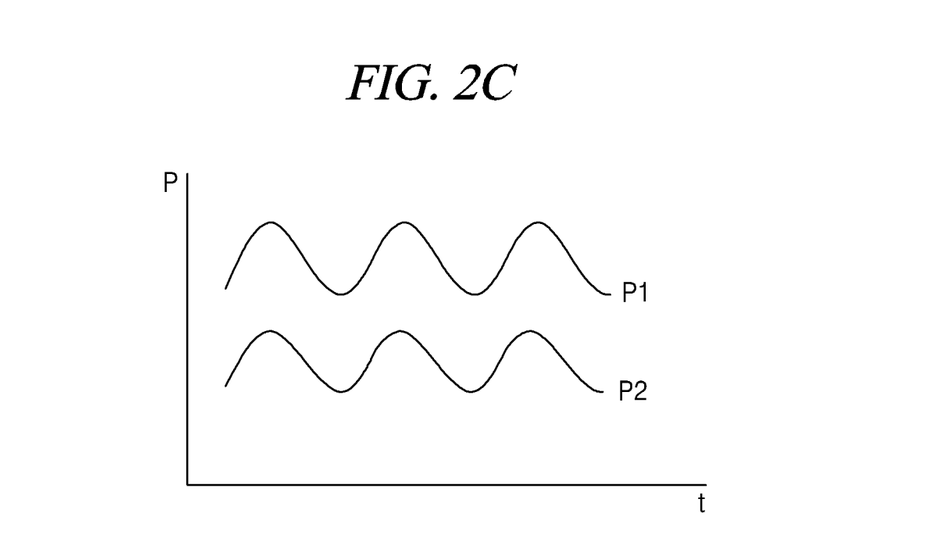

Meanwhile, FIG. 2c is a graph illustrating the pressures $P_1$ and $P_2$ measured by the sensor module 100 according to an embodiment of the present invention.

Figure 2D:
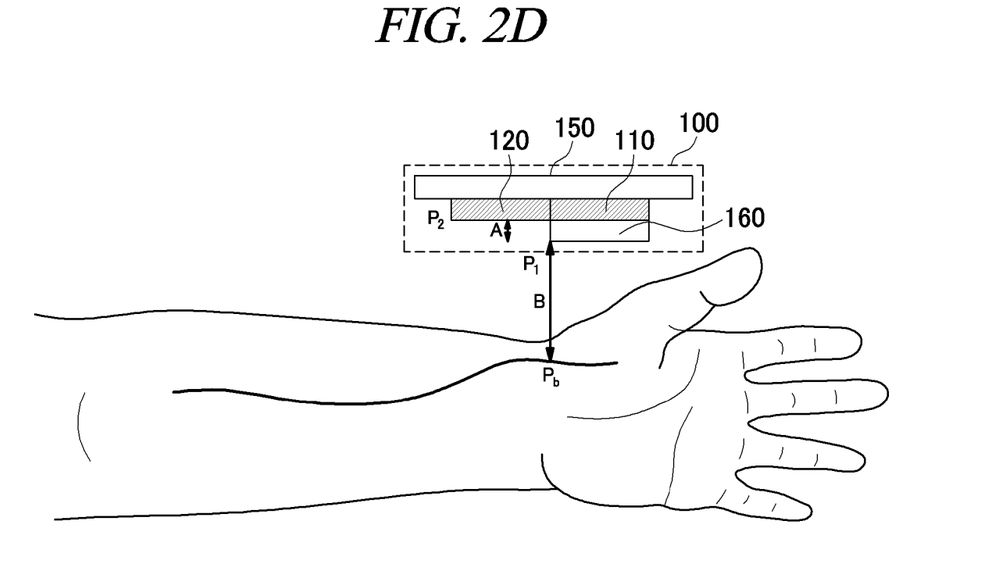
Figure 2E:
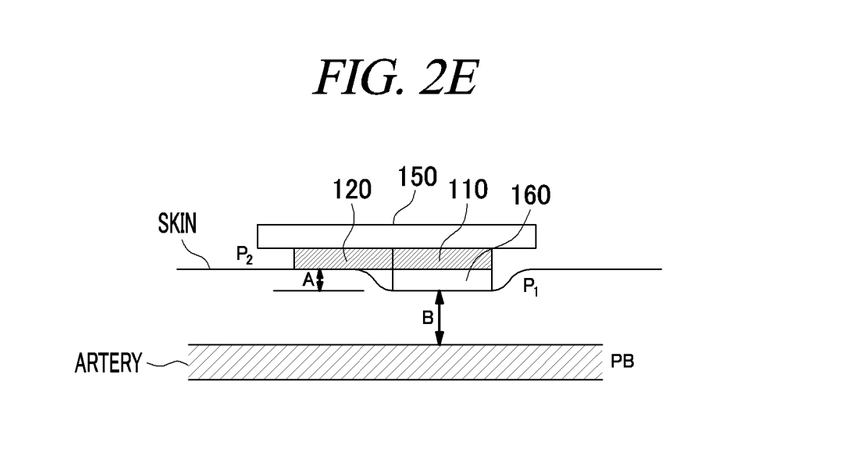

As an additional embodiment, the support unit 160 may be coupled to the upper portion of the first pressure sensor unit 110 as illustrated in FIGS. 2d and 2e. The support unit 160 is made of a rigid structure and the pressure of the contact portion is transmitted to the first pressure sensor unit 110 as it is. The support unit 160 is coupled to the upper portion of the first pressure sensor unit 110, so that a step of a first distance may be formed between the upper portion of the support unit 160 and the upper portion of the second pressure sensor unit 120. In this way, even in a case where the support unit 160 made of the rigid structure is disposed on the upper portion of any one sensor in a state where the sensors are disposed to have the same height, blood pressure measurement using the step between the sensors is possible as in the embodiment of FIG. 2a.

The control unit 130 may calculate the distance between the first pressure sensor unit 110 and the artery, and the blood pressure of the artery based on the pressures measured by the first pressure sensor unit 110 and the second pressure sensor unit 120, and the distance difference between the upper portion of the support unit 160 made of the rigid structure and the upper portion of the second pressure sensor unit 120. The above-mentioned upper portion may be the 6 o'clock direction of FIGS. 2d and 2e.

Referring to FIGS. 2d and 2e, the actual blood pressure of the artery to be measured is $P_b$, the pressure measured by the first pressure sensor unit 110 is $P_1$, the pressure measured by the second pressure sensor unit 120 is $P_2$, the distance from the upper portion of the support unit 160 made of the rigid structure to the upper portion of the second pressure sensor unit 120 is A, and the distance from the upper portion of the support unit 160 to the artery is B. In this case, the distance A is a predetermined constant value, $P_1$ and $P_2$ are the pressures measured by the sensor module 100, and the distance B and blood pressure $P_b$ are values output by calculation. In a case of the distance B, since it is the distance from the upper portion of the support unit 160 to the blood vessel inside the wrist, it is a value measured differently depending on the person.

The pressure measured by the sensor module 100 is inversely proportional to the distance between the blood vessel and the second pressure sensor unit 120, and the distance between the blood vessel and the support unit 160. Therefore, the distance B from the support unit 160 to the artery may be obtained by using Equation 1 above.

When the distance B from the upper portion of the support unit 160 to the artery is obtained, the blood pressure $P_B$ may also be obtained by using Equation 2 above.

Figure 3A:
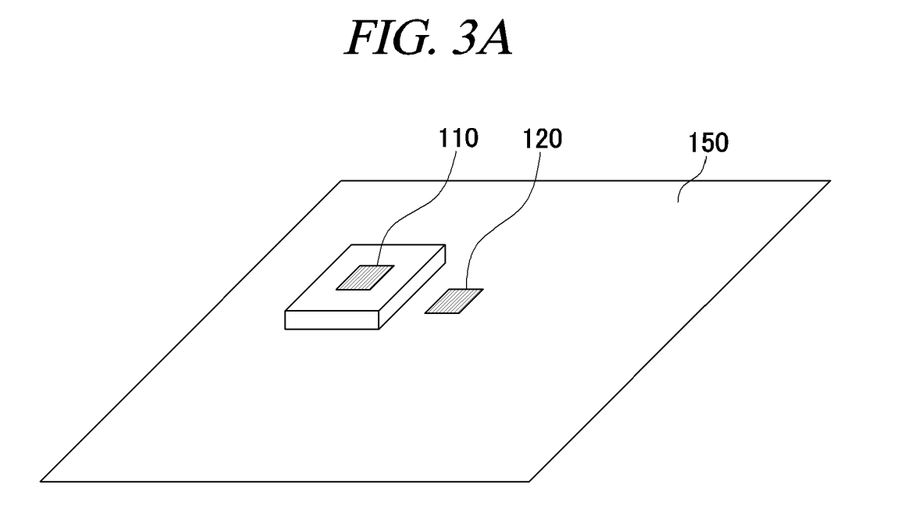
FIGS. 3a to 3f are perspective views for explaining a configuration of the sensor module according to an embodiment of the present invention.
Figure 3B:
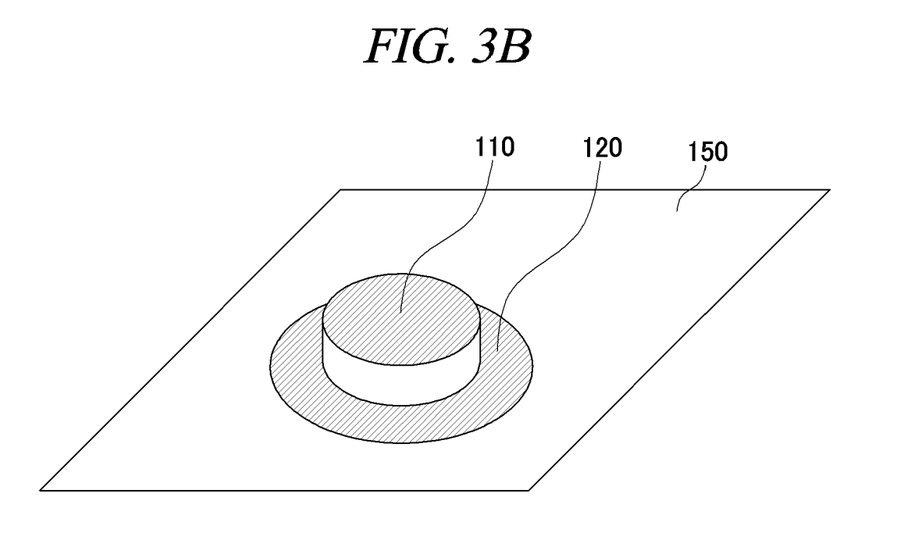
Figure 3C:
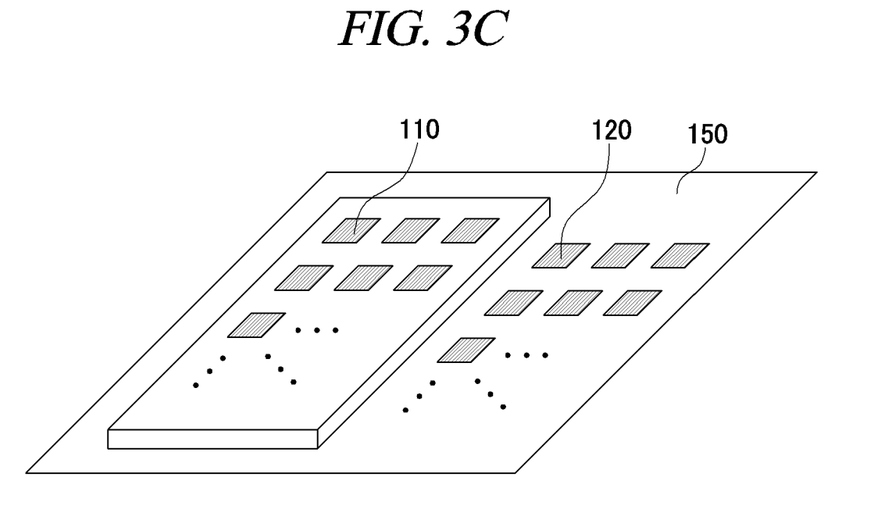

FIGS. 3a to 3c are perspective views for explaining the configuration of the sensor module according to an embodiment of the present invention.

The first pressure sensor unit 110 and the second pressure sensor unit 120 are disposed adjacent to each other, and protrude from the reference plane of the substrate unit 150 by different distances, to be located. As illustrated in FIG. 3a, the second pressure sensor unit 120 is located on the reference plane of the substrate unit 150, and the first pressure sensor unit 110 is located on a surface protruding from the substrate unit 150, so that when the sensor module 100 is attached to the wrist for measuring the blood pressure, the first pressure sensor unit 110 may be located closer to the blood vessel.

In addition, as illustrated in FIG. 3b, the first pressure sensor unit 110 may be located on a surface protruding from the center of the substrate unit 150 and the second pressure sensor unit 120 may be located on the reference plane of the substrate unit 150 in a form of surrounding the first pressure sensor unit 110. At this time, as illustrated in the drawing, the second pressure sensor unit 120 may be formed in a circular band shape surrounding the first pressure sensor unit 110. However, the second pressure sensor unit 120 is not limited to the circular shape and may be formed in other shapes.

In addition, as illustrated in FIG. 3c, the first pressure sensor unit 110 and the second pressure sensor unit 120 each may include a plurality of sensors disposed in an array form, the first pressure sensor unit 110 may be located on a surface protruding from the reference plane of the substrate unit 150, and the second pressure sensor unit 120 may be located on the reference plane of the substrate unit 150. In this case, the array disposition form of FIG. 3c may also be applied to the embodiment of FIG. 3b. That is, the first pressure sensor unit 110 and the second pressure sensor unit 120 of FIG. 3b may each include a plurality of sensors disposed in the array form.

Since the first pressure sensor unit 110 and the second pressure sensor unit 120 each measure the pressures with the plurality of sensors, a maximum value, a minimum value, a maximum frequency value (maximum value of frequency), or an average value of the pressures sensed by the sensors included in each of the pressure sensor units 110 and 120 may be specified and used as the first pressure and the second pressure, respectively when the blood pressure is calculated.

The disposition of the pressure sensor units 110 and 120 is not limited to the above embodiments and may be performed in various forms.

Figure 3D:
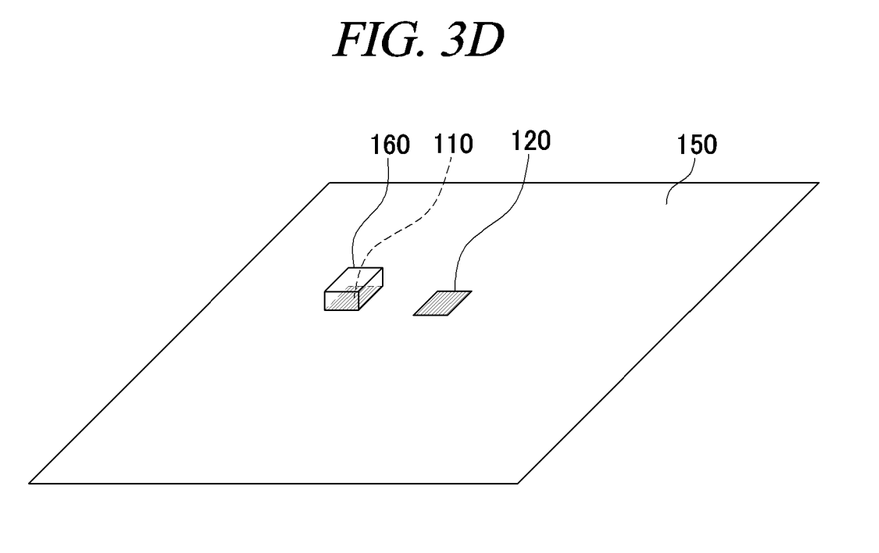
Figure 3E:
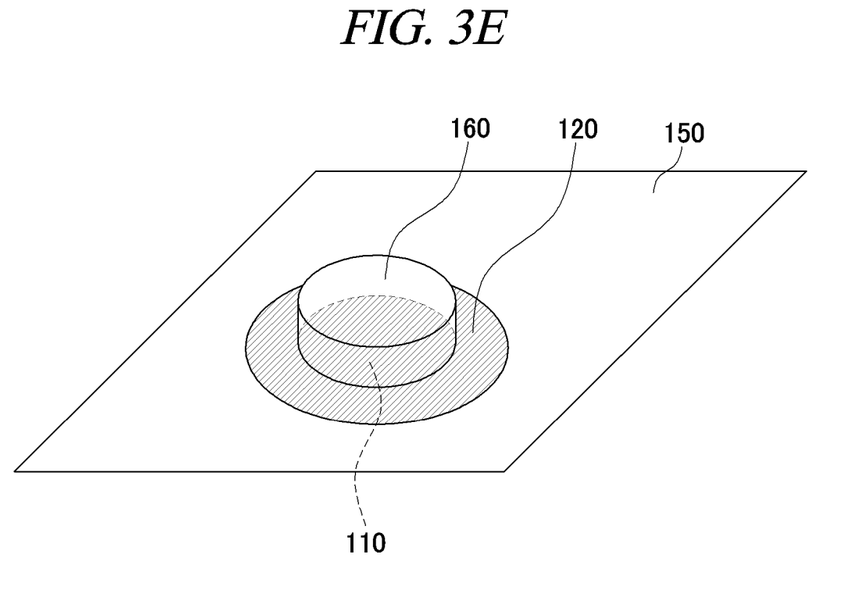
Figure 3F:
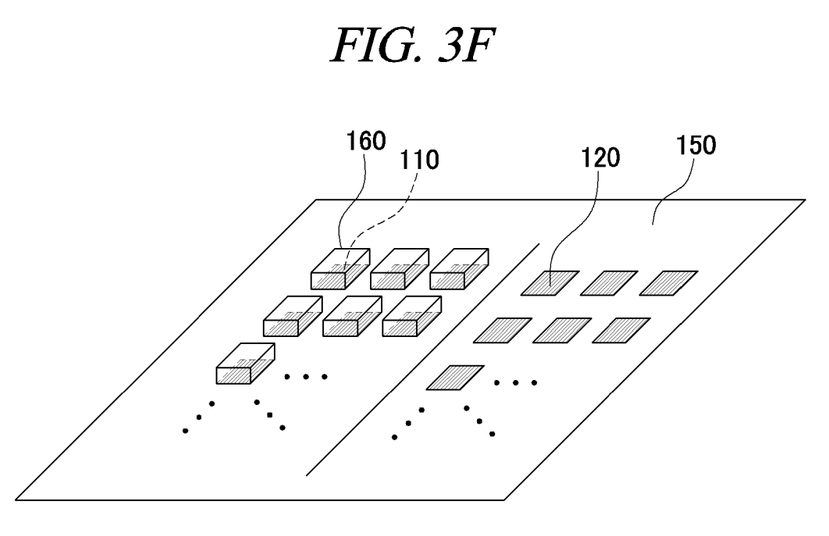

As an additional embodiment, FIGS. 3d to 3f are perspective views for explaining a configuration of the sensor module according to an embodiment of the present invention.

The first pressure sensor unit 110 and the second pressure sensor unit 120 are disposed adjacent to each other, and the support unit 160 made of the rigid structure is located on the upper portion of the first pressure sensor unit 110. As illustrated in FIG. 3d, the first pressure sensor unit 110 and the second pressure sensor unit 120 are located on the reference plane of the substrate unit 150, and the support unit 160 is located on the upper portion of the first pressure sensor unit 110. Therefore, when the sensor module 100 is attached to the wrist to measure blood pressure, the first pressure sensor unit 110 may measure the pressure at a position closer to the blood vessel.

In addition, as illustrated in FIG. 3e, the first pressure sensor unit 110 may be located at the center of the substrate unit 150 and the second pressure sensor unit 120 may be located on the reference plane of the substrate unit 150 in a form surrounding the first pressure sensor unit 110. In addition, the support unit 160 may be located on the upper portion of the first pressure sensor unit 110. At this time, as illustrated in the drawing, the second pressure sensor unit 120 may be formed in a circular band form surrounding the first pressure sensor unit 110. However, the second pressure sensor unit 120 is not limited to the circular shape and may be formed in other shapes.

In addition, as illustrated in FIG. 3f, the first pressure sensor unit 110 and the second pressure sensor unit 120 each include a plurality of sensors disposed in an array form, and the first pressure sensor unit 110 and the second pressure sensor unit 120 may be located on the reference plane of the substrate unit 150. The support unit 160 may be located above the plurality of first pressure sensor units 110, respectively. In this case, the array disposition form of FIG. 3f may also be applied to the embodiment of FIG. 3e. That is, the first pressure sensor unit 110 and the second pressure sensor unit 120 of FIG. 3e each may include a plurality of sensors disposed in the array form.

Since the first pressure sensor unit 110 and the second pressure sensor unit 120 each measure the pressures with the plurality of sensors, a maximum value, a minimum value, a maximum frequency value (maximum value of frequency), or an average value of the pressures sensed by the sensors included in each of the pressure sensor units 110 and 120 may be specified and used as the first pressure and the second pressure, respectively when the blood pressure is calculated.

The disposition of the pressure sensor units 110 and 120 is not limited to the above embodiment and may be disposed in various forms.

Figure 4A:
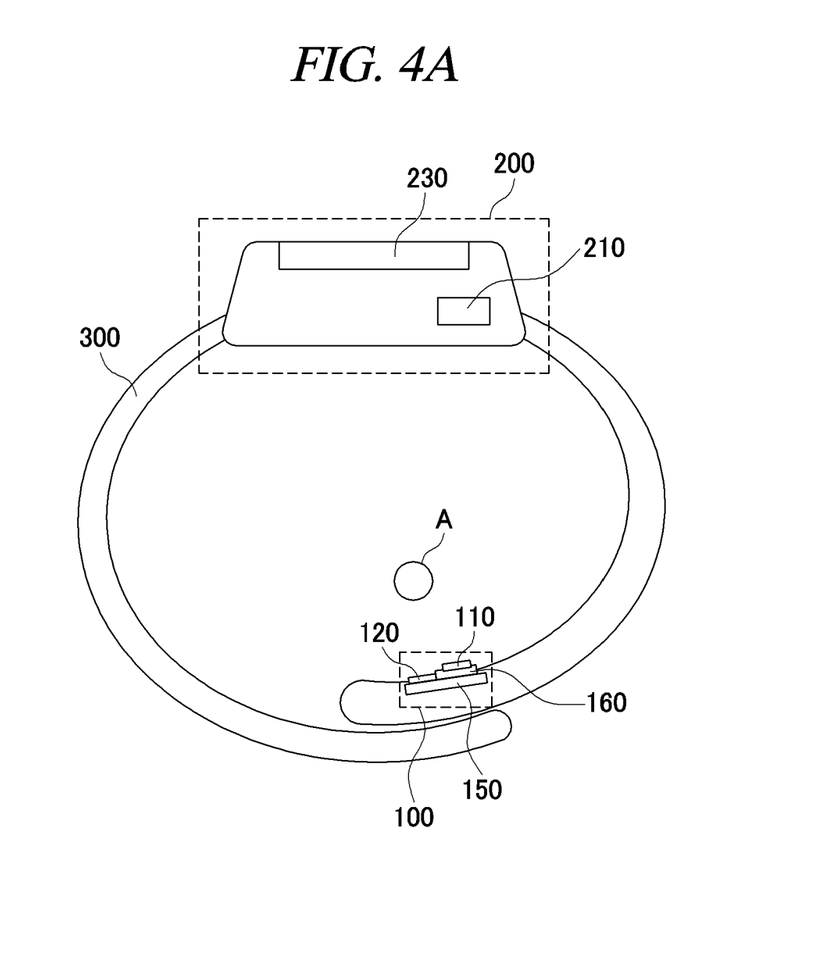
FIGS. 4a and 4b are sectional views illustrating a configuration of a wrist-worn portable blood pressure measuring device according to an embodiment of the present invention.

FIG. 4a is a sectional view illustrating a configuration of a wrist-worn portable blood pressure measuring device according to an embodiment of the present invention.

The wrist-worn portable blood pressure measuring device 10 includes the sensor module 100, the body unit 200, and the wrist strap 300. The body unit 200 is connected to the center of the wrist strap 300 and is configured to be worn on the wrist of the user. The display unit 230 is located on the outer surface of the wrist strap 300 so that the user may easily read the displayed information.

As described above, the portable blood pressure measuring apparatus 10 using the pressure sensor may be provided in a form of a wearable device worn on the wrist of the user or the like, and may be configured in various forms such as a wrist watch, a smart band or a bracelet to be worn on the wrist.

The power supply unit 210 may be configured as a built-in type in the body unit 200 or the wrist strap 300, or may be configured as a separate replaceable battery.

The portion A within the wrist is a position that should be considered to measure the blood pressure with the artery A. The sensor module 100 is formed in the wrist strap 300 at a position closely corresponding to the artery in a case where the user wears the portable blood pressure measuring device.

The sensor module 100 may be used by being coupled to the wrist strap 300 or the body unit 200. In the drawing, the sensor module 100 is coupled to one end of the wrist strap 300. In another embodiment, it may be implemented in a form of coupling the sensor module 100 to the lower surface of the body unit 200.

In a case where the user wears the portable blood pressure measuring device in the wrist strap 300, the sensor module 100 may be used separately from the body unit 200 to be formed at a position closely corresponding to the artery A. Since the support unit 160 is located on the substrate unit 150 in the sensor module 100, there is a step, the first pressure sensor unit 110 is located on the support unit 160, and the second pressure sensor unit 120 is located on the reference plane of the substrate unit 150. Accordingly, a difference in distance from the pressure sensor units 110 and 120 to the artery occurs, and the sensor module 100 may measure the blood pressure using the distance difference.

Figure 4B:
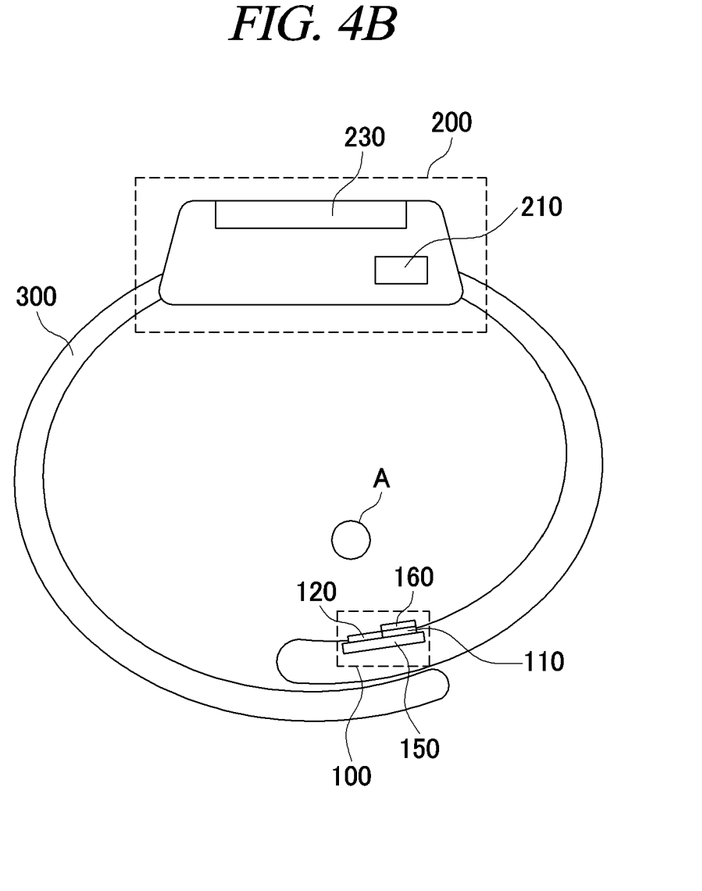

As an additional embodiment, as illustrated in FIG. 4b, in a case where the user wears the portable blood pressure measuring device, the sensor module 100 may also be used separately from the body unit 200 in the wrist strap 300 to be formed at a position closely corresponding to the artery. The first pressure sensor unit 110 and the second pressure sensor unit 120 may be located on the reference plane of the substrate unit 150, and the support unit 160 made of the rigid structure may be located in the upper portion of the first pressure sensor unit 110. Accordingly, a difference in distance from the upper portion of the support unit 160 and the upper portion of the second pressure sensor unit 120 to the artery may occur, and the sensor module 100 may measure the blood pressure using the distance difference.

Figure 5:
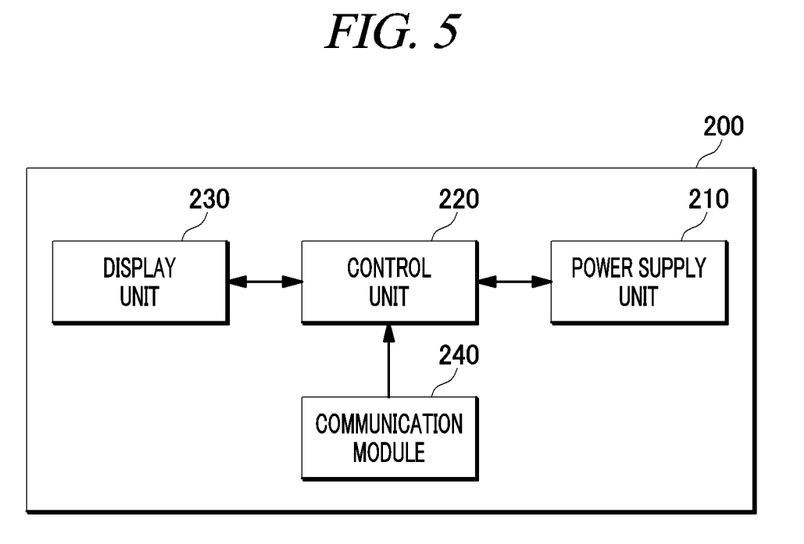
FIG. 5 is a block diagram illustrating a configuration of a body unit of a wrist-worn portable blood pressure measuring device according to an embodiment of the present invention.

FIG. 5 is a block diagram illustrating the body unit 200 of the portable blood pressure measuring device according to an embodiment of the present invention.

The body unit 200 may include the power supply unit 210, the control unit 220, the display unit 230, and the communication module 240.

The power supply unit 210 supplies power to the sensor module 100 and the body unit 200. For example, the power supply unit 210 may supply power to the sensor module 100 at the time of the blood pressure measurement and may cut off power, otherwise.

The control unit 220 controls the sensor module 100 to measure the blood pressure via the communication module 240 when blood pressure measurement is required, and displays the measured information on the display unit 230. For example, the blood pressure is measured in unit of time and the measured information is displayed on the display unit 230, and in a case where the blood pressure out of a preset range is measured, an alarm may be generated, or information thereof may be transmitted to a predetermined user by using the communication module 240. When the alarm is generated, the user may check the high blood pressure or low blood pressure state immediately.

The display unit 230 may be implemented as a display monitor of various types, such as a liquid crystal display, a reflective display, and an OLED display. The display unit 230 may display the blood pressure calculated by the control unit 220 or other information.

The communication module 240 may communicate with the communication module 140 of the sensor module 100 and various external devices (servers or terminals) in communication formats set respectively to transmit and receive data.

Figure 6:
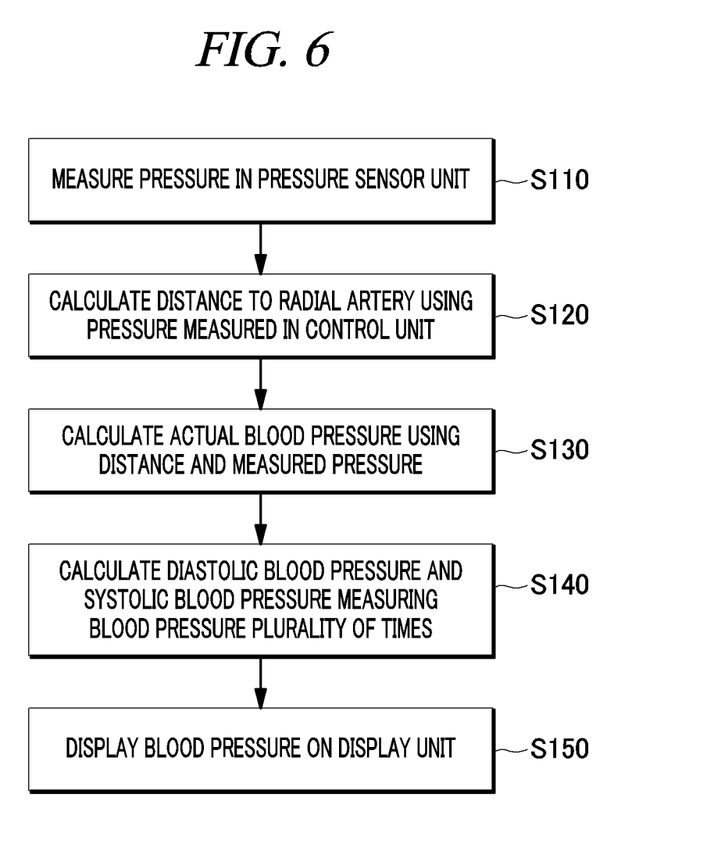
FIG. 6 is a flowchart of a blood pressure measuring method using a pressure sensor according to an embodiment of the present invention.

FIG. 6 is a flowchart illustrating a blood pressure measuring method using the pressure sensor according to an embodiment of the present invention.

First, the first pressure sensor unit 110 and the second pressure sensor unit 120 each measure the pressure at each position (S110). The measured pressure is a relative blood pressure that changes in inverse proportion to the distance from the artery A.

The control unit 130 receives the first pressure $P_1$ and the second pressure $P_2$ measured by the first pressure sensor unit 110 and the second pressure sensor unit 120, and uses the first pressure $P_1$ and the second pressure $P_2$ to calculate the distance B from the first pressure sensor unit 110 to the artery A (S120).

At this time, the distance B is calculated by using Equation 1 described above.

The control unit 130 uses the first pressure $P_1$ and the second pressure $P_2$, and the distance B from the first pressure sensor unit 110 to the artery A to calculate the actual blood pressure $P_B$ (S130).

At this time, the blood pressure is calculated by using Equation 2 described above.

In order to measure the diastolic blood pressure and the systolic blood pressure, respectively, a step of measuring the blood pressure a plurality of times may be further performed (S140). For example, after measurement at intervals of 10 ms for 10 seconds, an average of upper ten measured values may be determined as the systolic blood pressure, and an average of lower ten measured values may be determined as the diastolic blood pressure. In order to measure the blood pressure more accurately, the measurement interval may be 1 ms.

The control unit 220 displays information including the diastolic blood pressure and the systolic blood pressure on the display unit 230 (S150). At this time, in a case where the blood pressure is out of a preset normal range, an alarm for notifying the high or low blood pressure, and the like may be generated or an alarm message may be transmitted to another device such as a preset mobile phone.

Figure 7:
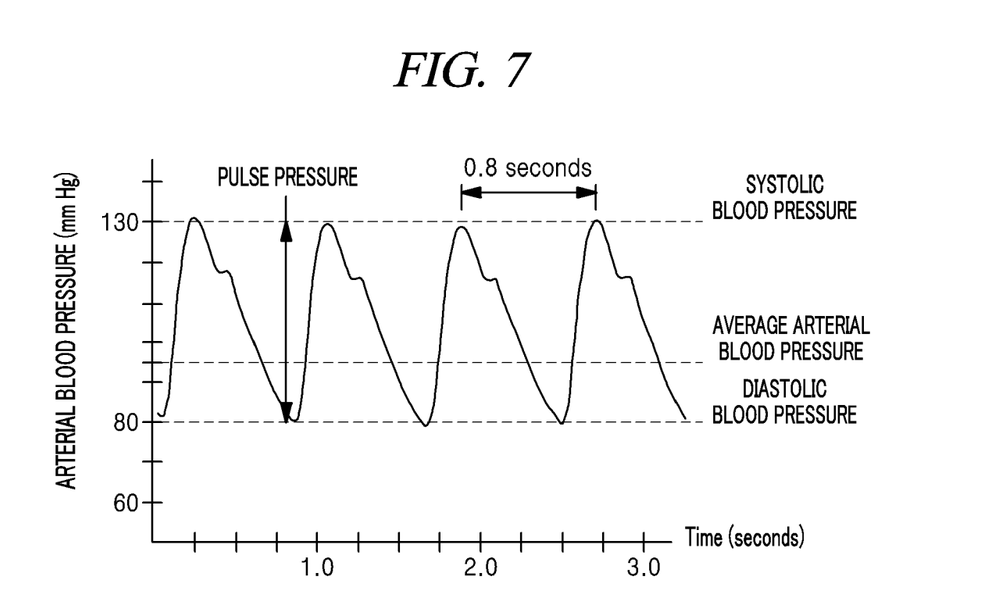
FIG. 7 is a view illustrating a graph of a change in an arterial blood pressure over time.

FIG. 7 is a graph illustrating a change in the arterial blood pressure over time, which may be referred to when determining the measurement interval for measuring the diastolic blood pressure and the systolic blood pressure.

An embodiment of the present invention may also be implemented in a form of a recording medium including instructions executable by a computer, such as a program module executed by a computer. Computer-readable media may be any available media that may be accessed by a computer and includes all of volatile and nonvolatile media, and removable and non-removable media. Also, the computer-readable media may include computer storage media. Computer storage media includes all of volatile and non-volatile media, and removable and non-removable media implemented in any method or technology for storage of information such as computer readable instructions, data structures, program modules or other data.

Although the methods and systems of the present invention have been described with reference to specific embodiments, some or all of their configuration elements or operations may be implemented by using a computer system having a general purpose hardware architecture.

The above description of the present application is for illustration and those of ordinary skill in the art to which the present application pertains will understand that it may be easily modified into other specific forms without changing the technical spirit or essential features of the present application. Therefore, it should be understood that the embodiments described above are illustrative in all respects and not restrictive. For example, each configuration element described as a single type may be implemented in a dispersed form, and likewise configuration elements described as distributed may be implemented in a combined form.

The scope of the present application is indicated by the following claims rather than the above detailed description, and all changes or modifications derived from the meaning and scope of the claims and their equivalent concepts should be construed as being included in the scope of the present application.

REFERENCE SIGNS LIST

10: portable blood pressure measuring device using pressure sensor
100: sensor module for blood pressure measurement
110: first pressure sensor unit
120: second pressure sensor unit
130: control unit
140: communication module
150: substrate unit
160: support unit (or support unit made of rigid structure)
200: body unit
210: power supply unit
220: control unit
   230: display unit
   240: communication module
   300: wrist strap

The invention claimed is:

1. A sensor module for blood pressure measurement, comprising:
a substrate unit;
a first pressure sensor unit disposed on a reference plane of the substrate unit and configured to measure a first pressure;
a second pressure sensor unit disposed adjacent to the first pressure sensor unit on the reference plane and configured to measure a second pressure, wherein the first pressure sensor unit and the second pressure sensor unit protrude by different distances from the reference plane and form a step of a first distance between an upper portion of the first pressure sensor unit and an upper portion of the second pressure sensor unit; and
a control unit configured to operate the first pressure sensor unit and the second pressure sensor unit; estimate a second distance from the upper portion of the first pressure sensor unit and a target blood vessel by using the first pressure, the second pressure and the first distance;
and calculate a blood pressure value in the target blood vessel based on the second distance, the first pressure and the second pressure.

2. The sensor module of claim 1, further comprising:
a support unit disposed between a lower portion of the first pressure sensor unit and the reference plane of the substrate unit.

3. The sensor module of claim 1, wherein the control unit is configured to calculate the blood pressure value in the target blood vessel by multiplying the first pressure by the second distance, or multiplying the second pressure by a sum of the first distance and the second distance.

4. The sensor module of claim 1, wherein the first distance is a distance between a reference plane of the first pressure sensor unit and a reference plane of the second pressure sensor unit.

5. The sensor module of claim 1,
wherein the first pressure sensor unit or the second pressure sensor unit is a strain gauge-based semiconductor thin film sensor, a capacitive thin film sensor for detecting a capacitance change according to a pressure, or a piezoresistive sensor using a piezo resistance effect.

6. The sensor module of claim 1,
wherein the second pressure sensor unit surrounds the first pressure sensor unit.

7. The sensor module of claim 1,
wherein the first pressure sensor unit and the second pressure sensor unit each includes a plurality of sensors disposed in an array form.

8. The sensor module of claim 1,
wherein the first pressure sensor unit and the second pressure sensor unit each includes a plurality of sensors disposed in an array form, and
wherein the control unit is configured to specify a maximum value, a minimum value, a maximum frequency value, or an average value of pressures sensed by the sensors included in the first pressure sensor unit as the first pressure, and a maximum value, a minimum value, a maximum frequency value, or an average value of pressures sensed by the sensors included in the second pressure sensor unit as the second pressure.

9. A wrist-worn portable blood pressure measuring device comprising:
  a body unit in which a display unit displaying blood pressure value, a power supply unit, and a control unit are built;
  a wrist strap coupled to the body unit; and
  a sensor module,
  wherein the sensor module comprises:
  a substrate unit;
  a first pressure sensor unit disposed on a reference plane of the substrate unit and configured to measure a first pressure;
  a second pressure sensor unit disposed adjacent to the first pressure sensor unit on the reference place and configured to measure a second pressure, wherein the first pressure sensor unit and the second pressure sensor unit protrude by different distances from the reference plane and form a step of a first distance between an upper portion of the first pressure sensor unit and an upper portion of the second pressure sensor unit; and
  the control unit configured to operate the first pressure sensor unit and the second pressure sensor unit; estimate a second distance from the upper portion of the first pressure sensor unit and a target blood vessel by using the first pressure, the second pressure and the first distance; and calculate the blood pressure value in the target blood vessel based on the second distance, the first pressure and the second pressure, and
  wherein the sensor module is coupled to the body unit or the wrist strap.

10. The portable blood pressure measuring device of claim 9, further comprising:
  a communication module for performing data communication,
  wherein the control unit is configured to transmit the blood pressure value to an external device via the communication module.

* * * * *